United States Patent [19]

Canavesi et al.

[11] 4,420,421

[45] Dec. 13, 1983

[54] PROCESS FOR THE PREPARATION OF CATALYSTS BASED ON IRON AND MOLYBDENUM OXIDES

[75] Inventors: Roberto Canavesi, Arese; Giancarlo Aglietti, Milan; Roberto Ghezzi, Cusano Milanino, all of Italy

[73] Assignee: Euteco Impianti S.p.A., Milan, Italy

[21] Appl. No.: 326,623

[22] Filed: Dec. 2, 1981

[30] Foreign Application Priority Data

Dec. 2, 1980 [IT] Italy ............................ 26348 A/80

[51] Int. Cl.$^3$ ............................................. B01J 23/88
[52] U.S. Cl. ................................................... 502/316
[58] Field of Search ........................................ 252/470

[56] References Cited

U.S. PATENT DOCUMENTS 2,812,309 11/1957 Allyn et al. ........................ 252/470
3,489,692 1/1970 Bourne et al. .................. 252/466 B Primary Examiner—W. J. Shine
Attorney, Agent, or Firm—Sughrue, Mion, Zinn, Macpeak & Seas

[57] ABSTRACT

A process is described for the preparation of catalysts based on molybdenum and iron oxides which comprises their controlled precipitation in an aqueous medium from sodium molybdate and a soluble ferric salt, the separation and the washing of the precipitate until its sodium content is reduced to less than 150 ppm. According to one embodiment, the sodium molybdate used as the reagent results from the action of aqueous sodium hydroxide on the spent catalyst.

6 Claims, No Drawings

PROCESS FOR THE PREPARATION OF CATALYSTS BASED ON IRON AND MOLYBDENUM OXIDES

The present invention relates to improvements in processes for the preparation of catalysts based on iron and molybdenum oxides, and optionally, cobalt or nickel oxides as well, which are active in the production of formaldehyde by the oxidation of methanol.

Catalysts for the oxidation of methanol which are based on iron and molybdenum oxides are known in the art and have been described in U.S. Pat. No. 1,913,405. These catalysts, as is known, have a considerable tendency to break down and, in order to overcome this disadvantage, it has been proposed to form an inactive precursor for the catalyst with physical properties which allow it to be transported and loaded into the reactor for use. The catalyst is activated within the reactor by heating to a high temperature in the presence of air. It has also been proposed to use a support for the catalyst and, more precisely, a sintered iron oxide or metal carbide support, generally silicon carbide. For a better understanding reference should be made to the specifications of U.S. Pat. Nos. 2,812,308 and 2,812,309.

At present it is common practice to prepare molybdenum- and iron-oxide-based catalysts by means of a process which comprises, essentially, the following steps carried out in succession:

precipitation in an aqueous medium from ammonium paramolybdate and a soluble ferric iron salt;

separation and washing of the precipitate and reduction of the water content of the washed precipitate;

conversion of the solid obtained into bodies of suitable form and dimensions;

drying the bodies obtained and calcining them at high temperature.

The processes described in the Patents given below are based on such a general scheme:

Canada No. 619,043 in which, inter alia a particular treatment of the solid in the plastic state is described in a step preceding the heat treatment;

U.S. Pat. No. 3,459,807 which describes inter alia, the reduction of the water content of the washed, precipitated solid by means of a pressing treatment;

Belgian No. 601,600 which teaches, inter alia, the addition of small quantities of cobalt oxide to the molybdenum and iron oxides;

U.S. Pat. No. 3,464,931 which describes, inter alia, the formation of the dried solid into tablets in the form of hollow cylinders.

The general use of ammonium paramolybdate as the molybdenum reagent in the precipitation of the iron and molybdenum oxides is due essentially to the fact that the ammonium salts of the molybdenum heteropolyacids, which may form during the precipitation, are easily decomposed during the thermal treatment of the catalysts with consequent evolution of gaseous ammonia.

Thus it is possible to obtain catalysts constituted exclusively or almost exclusively by iron and molybdenum oxides. However, the use of the ammonium salt has disadvantages both due to the evolution of ammonia during the thermal treatment of the catalyst and as a result of the ammonium content of the liquors resulting from the precipitation and washing of the precipitate. According to the current regulations, these liquors must be treated to remove their ammonium content before being discharged.

In accordance with the process outlined above, the use of sodium molybdate in place of ammonium paramolybdate as the molybdenum reagent in the precipitation of iron and molybdenum oxides has not until now taken place, mainly because of the difficulties in obtaining a catalyst free, or substantially free, from sodium. Indeed it is known that sodium catalyses the combustion of methanol to form carbon oxides and water, with consequent reduction of the yield of formaldehyde.

With regard to this suggestion, it should be noted that there is no possibility of removing the sodium by volatilization during the thermal treatment of the catalyst, in which feature sodium differs from the ammonium ions which are volatilized during this treatment in the form of ammonia. On the other hand the use of sodium molybdate in the preparation of the catalysts under discussion would be desirable in view of the nonpolluting characteristics of the mother liquors from the precipitation and washing of the precipitate. Moreover, it is known that molybdenum is recovered from exhausted iron- and molybdenum-oxide-based catalysts in the form of aqueous sodium molybdate, by reaction of the catalysts themselves with aqueous sodium hydroxide solutions.

The direct use of these solutions resulting from the alkaline attack on the spent catalysts gives indubitable economic advantages.

It has now been found that it is possible to prepare iron- and molybdenum-oxide-based catalysts, which are active in the oxidation of methanol to formaldehyde, with scarcely any tendency toward the combustion of the methanol, from sodium molybdate and a soluble ferric salt. The present invention is based essentially on the discovery of conditions within which it is possible to obtain a precipitate of iron and molybdenum oxides, free or substantially free from sodium, while using sodium molybdate as molybdenum reagent.

The precipitate is then converted, by the usual methods, into the final active catalyst with a low activity towards the combustion of the methanol.

Accordingly, in the present invention catalysts based on iron and molybdenum oxides are prepared by means of a process characterised in that an aqueous solution of a soluble ferric salt is brought into contact with a sodium molybdate aqueous solution having a pH value within the range 5.0 to 5.5 and a molybdenum content of about 32 to 33 g/liter; the molar ratio of molybdenum, as $MoO_3$, to the iron, as $Fe_2O_3$, being greater than 2/1 and the precipitate obtained is then washed with de-ionized water until sodium is absent or substantially absent from the washing water.

Outside the said pH range, it is impossible to remove by water washing the sodium salts from the precipitate down to a level where the catalytic action of sodium is not more causing an excessive reduction of the yield of formaldehyde.

The reason of this impossible is attributed to the formation, during the precipitation step, of a modified crystalline form of the precipitate occluding sodium as an insoluble salt.

The aqueous solutions of sodium molybdate which are suitable for the purposes of the present invention may be obtained in various manners.

For example, the treatment of exhausted catalysts containing molybdenum in the form of its oxide, together with oxides of other metals such as iron and cobalt, with aqueous sodium hydroxide, allows solutions of sodium molybdate with a pH which is typically of the order of 10.8 to 11 to be obtained. At this pH the hydrated oxides of the other metals mentioned above are, in fact, precipitated.

According to the present invention, a mineral acid is added to these solutions to bring their pH to values within the range 5.0 to 5.5, with a molybdenum concentration, evaluated in terms of the metal, of the order of 32 to 33 f/liter.

Mineral acids which are suitable for the purpose are hydrogenchloride and nitric acid, the first being preferred to the second. It is also possible to use sulphuric acid for this purpose although this acid is less preferable than the two mentioned above.

When $MoO_3$ free from other metal oxides is used in the prepartion of the solution of the molybdenum salt, it is possible to meter the quantity of sodium hydroxide used for the reaction, as well as the concentration of the sodium hydroxide, so as to give an aqueous solution of the molybdenum salt with a pH equal to or close to the final desired pH for a molybdenum content within the range of values indicated above.

A further method of obtaining the solutions under discussion consists of dissolving a sodium salt of molybdenum (for example sodium dimolybdate) in water until the stated molybdenum concentration is achieved and then correcting the pH of the solution to the desired value by means of cited mineral acids.

According to another embodiment, the liquors resulting from the precipitation and/or washing of the molybdenum and iron oxides are treated with an anionic exchange resin which is weakly salified with acid so as to bind the molybdenum ions on to the resin itself. The molybdenum ions are then recovered in the form of aqueous sodium molybdate by treatment of the resin containing the molybdenum ions by means of an aqueous sodium hydroxide solution. The solution thus obtained is suitable for the purposes of the present invention after treatment to bring the molybdenum content and the pH values within the ranges stated above.

In the preferred embodiment, the pH is corrected to a value in the range 5.2 to 5.3, the sodium molybdate solution still having a molybdenum content (in terms of the metal) of about 32–33 g/liter.

Water-soluble iron salts which are useful for the purposes of the present invention are those in which the iron is trivalent. Among these the preferred salt is ferric chloride, particularly suitable as aqueous solutions with a salt concentration of from 20 to 70 g/liter.

In the preferred embodiment, the aqueous solution of the molybdenum salt is heated to a temperature of the order of 50° C. and the aqueous solution of the ferric salt, at room temperature (20°–25° C.) is poured into the said solution. The mixture obtained is then heated to about 50° C. It is preferable to keep the mass stirred during these operations. Thus a precipitate is formed which, after cooling, is separated by decantation, filtration, centrifuging or the like, and is then washed until the washing water is free, or substantially free, from sodium (sodium content less than about 150 ppm). This washed precipitate is converted into the active catalyst by conventional methods and the said catalyst typically has a sodium content less than or equal to about 150 ppm.

With regard to the conversion of the washed precipitate into the final active catalyst, this is usually carried out by reducing the water content of the precipitate then converting the precipitate into bodies of a suitable form and size and finally activating it at high temperatures, generally within the range 300° to 450° C. More particularly, this may be carried out in the following manner:

the water content of the washed precipitate is reduced to 20 to 40% by weight by filtration and pressing to form a panel;

this panel is ground to form granules;

the granules are dried by gradual heating at a temperature below 100° C.;

the dried granules are calcined by gradual heating to a temperature less than or equal to 450° C.

The $MoO_3/Fe_2O_3$ molar ratio in these catalysts is usually kept in the range 2.1/1 to 3.5/1.

According to a different method, a catalyst containing cobalt oxide in addition to the molybdenum and iron oxides is prepared and the said catalyst is converted into tablets with holes. More particularly, this is carried out as follows:

the washed precipitate of the molybdenum and iron oxides is homogenized with a precipitated containing molybdenum and cobalt oxides obtained in a similar manner;

the water content of the homogenized precipitate is reduced to 30–40% by weight so as to form a conglomerate;

the conglomerate is ground to a particle size of about 0.3 to 0.85 mm;

the particles are dried at a temperature of up to 100° C. so as to reduce the water content further to values of 5–10% by weight;

the dried particles are formed into hollow, cylindrical tablets;

the hollow cylinders are calcined.

The $MoO_3/Fe_2O_3$ ratio maintained in these catalysts is usually from 4/1 to 6/1 and the $MoO_3/CoO$ ratio is usually from 30/1 to 70/1.

The above two methods of carrying out the process have been given purely by way of non-limiting example since they do not constitute a basic aspect of the present process.

Furthermore, it is possible to introduce inert material, for example titanium dioxide or active earths such as that known commercially by the name Florex, into the catalysts. The said inert material is preferably introduced in the form of a fine powder (granules with dimensions of the order of 1–30 microns) which is homogenized with the precipitated and washed metal oxides. The quantity of the support is not critical and may be up to a percentage of the order of 50% by weight in the final catalyst.

The catalysts of the present invention are used in the form of a fixed bed in the process of oxidizing methanol to formaldehyde. More particularly, in the said process a gaseous flow containing from 3–15% by volume of methanol and from 5–20% by volume of oxygen, the remaining percentage being constituted by inert gases is fed to the catalysts and the reaction is carried out at a temperature of from 300°–400° C. and with a volume rate of from 4000 to 15000 volumes of gas (under normal conditions) per volume of catalyst per hour. Under these conditions, a methanol conversion generally greater than 95% is achieved, with a selectivity towards the formaldehyde greater than or equal to 97% of the methanol converted.

The experimental examples which follow are illustrative and non-limiting of the invention.

EXAMPLE 1

Molybdenum is recovered from an exhausted catalyst based on molybdenum, iron and cobalt oxides, used in the oxidation of methanol to formaldehyde.

More particularly, 3,015 g of exhausted catalyst ($MoO_3$ content 2,443 g corresponding to a Mo content of 1,628 g) are treated with a solution of 1,357 g of NaOH in 14 liters of de-ionized water.

In this treatment, the exhausted catalyst is poured into the aqueous sodium hydroxide solution and the mass is kept stirred for three hours. The temperature rises spontaneously to about 45° C.

At the end of this treatment, the solid, consisting essentially of hydrated iron and cobalt oxides, is filtered off and washed with de-ionized water. The filtrate and the washing liquors are combined and a total of 16.24 liters of an aqueous sodium molybdate solution ($Na_2MoO_4$), with a Mo content of 1,628 g corresponding to a content of 2,443 g of $MoO_3$, is obtained.

To 16.24 liters of the aqueous sodium molybdate solution prepared in the manner indicated above, having a pH value of 10.2, are added 30 liters of de-ionized water. Then an aqueous 5% by weight solution of hydrochloric acid is added to bring the pH to 5.3. About three liters of the de-ionized water are then added to bring the Mo content of the solution to 32.6 g/liter (in terms of the metal), corresponding to a $MoO_3$ concentration of 48.92 g/liter.

The solution obtained is heated to 50° C., then a cold solution of 1,650 g of $FeCl_3.6H_2O$ in 33 liters of de-ionized water is added. Thus a precipitate is formed and the mass is heated to 50° C. under agitation. When the said temperature has been reached the agitation is stopped and the precipitation is allowed to settle. After 24 hours, the mother liquor is siphoned off, a volume of de-ionized water about equal to that removed is added and is agitated to redisperse the precipitate which is finally left to settle. This operation is repeated a further four times and the chloride and sodium ion content of the final liquid discharged is less than 0.1 g/liter. After these washings, the quantity of residual sodium in the precipitate is less than 150 ppm.

At this point the precipitate, comprising iron and molybdenum oxides, is filtered off and cobalt molybdate is added in such quantity as to give a CoO content of 2% by weight of the total solid content of the mixture.

After homogenization, the mixture is pressed to reduce its water content to values of the order of 30-40% by weight and the mass obtained is ground to form particles of a size of the order of 0.3 to 0.85 mm. The particles are dried by heating to a maximum temperature of 100° C. and, after homogenization with 1% by weight of magnesium stearate, are compressed into tablets in the form of hollow cylinders with a diameter and height of about 4.5 mm and with a bore diameter of about 2 mm.

Finally these are calcined by heating to a temperature of up to 420° C.

In the oxidation of methanol to formaldehyde, with carburation of the methanol equal to 6.5 in the gaseous flow which is supplied at a volume rate of 10,000 and with a temperature of the gaseous flow at the outlet from the reactor of 300° C., a conversion of the methanol to formaldehyde of 94% is achieved with a selectivity of 97.5%, the said conversion and selectivity values being given on a molar basis.

EXAMPLE 2

2.44 kg of $MoO_3$ are suspended in 50 liters of de-ionized water containing 0.58 kg of sodium hydroxide. Thus a solution is formed with a molybdenum content of 32.5 g/liter and with a pH value of 5.35 to 5.4.

The solution of the molybdenum salt prepared in the manner indicated above is heated to 50° C. and a solution of 1.65 kg of $FeCl_3.6H_2O$ in 33 liters of de-ionized water is added. The resulting mixture is heated to 50° C. and left to rest for 24 hours.

The preparation of the catalyst is then carried out as explained in Example 1.

In the oxidation of methanol to formaldehyde, under the conditions of example 1, the catalyst gives a 93% molar conversion of methanol to formaldehyde, with a selectivity of 97% molar.

EXAMPLE 3

2.97 kg of sodium dimolybdate are dissolved in 50 liters of de-ionized water and a solution is obtained with a pH of 5.5. To this solution is added an aqueous, 30% by weight solution of hydrochloric acid until a solution with a pH of 5.3 is obtained. This solution, which has a Mo content of 32.5 g/liter, is heated to 50° C. and a solution of 1.65 kg of $FeCl_3.6H_2O$ in 33 liters of de-ionized water is added. The resulting mixture is heated to 50° C. and then left to rest for 24 hours.

The preparation of the catalyst is then carried out as explained in Example 1.

In the oxidation of methanol to formaldehyde under the conditions of Example 1, the catalyst gives a 91.9% molar conversion of methanol to formaldehyde with a selectivity of 97.4% molar.

We claim:

1. Process for the preparation based on iron and molybdenum oxides, which are active in the oxidation of methanol to formaldehyde, characterised in that an aqueous solution of a soluble ferric salt is brought into contact with an aqueous solution of sodium molybdate having a pH value within the range 5.2 to 5.5 and a molybdenum content of about 32 to 33 g/liter; the molar ratio of the Molybdenum, as $MoO_3$, to iron, as $Fe_2O_3$, being greater than 2:1; the precipitate obtained is then washed with de-ionized water until the sodium content of the precipitate is equal or less than 150 ppm, the washed precipitate is then treated by known methods to obtain the final active catalyst.

2. Process according to claim 1, characterised in that the aqueous sodium molybdate solution is obtained by reacting aqueous sodium hydroxide with spent catalysts containing molybdenum oxide and the pH value of the aqueous solution of sodium molybdate after separation of solid precipitate is brought to from 5.2 to 5.5 by a mineral acid.

3. Process according to claim 1, characterised in that the aqueous sodium molybdate solution is obtained by treating the liquors formed in the precipitation and/or in the washing steps of the preparation of iron/molybdenum oxides catalysts with a weak anionic exchange resin so as to bind the molybdenum ions to the resin and then eluting the resin with aqueous sodium hydroxide and bringing the pH value of the solution to from 5.2 to 5.5 by a mineral acid.

4. Process according to claim 2 or to claim 3, characterised in that the mineral acid is hydrogen chloride, or nitric or sulphuric acid.

5. Process according to claim 1, charaterised in that said aqueous ferric chloride solution has a concentration from 20 to 70 g of $FeCl_3.6H_2O$ per liter.

6. The process according to claim 1 wherein the pH value of the aqueous solution of sodium molybdate is 5.2 to 5.3.

* * * * *